(12) United States Patent
Chadeayne

(10) Patent No.: US 12,343,328 B2
(45) Date of Patent: Jul. 1, 2025

(54) DIALKYL TRYPTAMINES AND THEIR THERAPEUTIC USES

(71) Applicant: CAAMTECH, INC., Issaquah, WA (US)

(72) Inventor: Andrew R Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 0 days.

(21) Appl. No.: 18/256,570

(22) PCT Filed: Dec. 8, 2021

(86) PCT No.: PCT/US2021/062331
§ 371 (c)(1),
(2) Date: Jun. 8, 2023

(87) PCT Pub. No.: WO2022/125616
PCT Pub. Date: Jun. 16, 2022

(65) Prior Publication Data
US 2024/0025850 A1    Jan. 25, 2024

Related U.S. Application Data

(60) Provisional application No. 63/123,203, filed on Dec. 9, 2020, provisional application No. 63/248,033, filed on Sep. 24, 2021.

(51) Int. Cl.
*A61K 31/4045*    (2006.01)
*C07D 209/16*    (2006.01)

(52) U.S. Cl.
CPC ........ *A61K 31/4045* (2013.01); *C07D 209/16* (2013.01)

(58) Field of Classification Search
CPC .......................... A61K 31/4045; C07D 209/16
See application file for complete search history.

(56) References Cited

U.S. PATENT DOCUMENTS

| 3,078,214 | A | 2/1963 | Hofmann et al. |
| 2008/0293695 | A1 | 11/2008 | Bristol et al. |
| 2012/0295946 | A1 | 11/2012 | Greig et al. |
| 2018/0021326 | A1 | 1/2018 | Stamets |
| 2018/0221396 | A1 | 8/2018 | Chadeayne |
| 2019/0142851 | A1 | 5/2019 | Chadeayne |
| 2023/0241027 | A1 | 8/2023 | Chadeayne |
| 2023/0295086 | A1 | 9/2023 | Grill |
| 2023/0346747 | A1 | 11/2023 | Chadeayne |

FOREIGN PATENT DOCUMENTS

| CZ | 307719 B6 | 3/2019 |
| GB | 2571696 A | 9/2019 |
| KR | 20230054397 A | 4/2023 |
| WO | 1994/014770 A1 | 7/1994 |
| WO | 2000/034242 A1 | 6/2000 |
| WO | 2009102805 A1 | 8/2009 |
| WO | 2013/063492 A1 | 5/2013 |
| WO | 2013/150529 A2 | 10/2013 |
| WO | 2016/161138 A1 | 10/2016 |
| WO | 2019/081764 A1 | 5/2019 |
| WO | 2019099745 A1 | 5/2019 |
| WO | 2020157569 A1 | 8/2020 |
| WO | 2020/181194 A1 | 9/2020 |
| WO | 2021108911 A1 | 6/2021 |
| WO | 2022/038299 A1 | 2/2022 |

OTHER PUBLICATIONS

Carhart-Harris, R. L. & Goodwin, G. M. (2017). Neuropsychopharmacology, 42, 2105-2113.

(Continued)

*Primary Examiner* — Kamal A Saeed
(74) *Attorney, Agent, or Firm* — RAPHAEL BELLUM PLLC

(57) ABSTRACT

The disclosure relates to a compound of formula (I): The disclosure also relates to a compound of formula (Ia): The disclosure relates to compositions comprising, consisting essentially of, or consisting of a compound of formula (I) or formula (Ia) and an excipient. The disclosure also relates to pharmaceutical compositions comprising a therapeutically effective amount of a compound of formula (I) or formula (Ia) where the excipient is a pharmaceutically acceptable carrier. The disclosure further relates to therapeutic uses of compounds of formula (I) or formula (Ia).

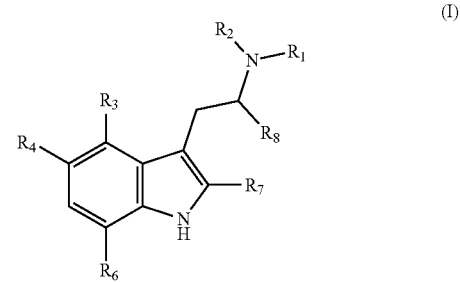

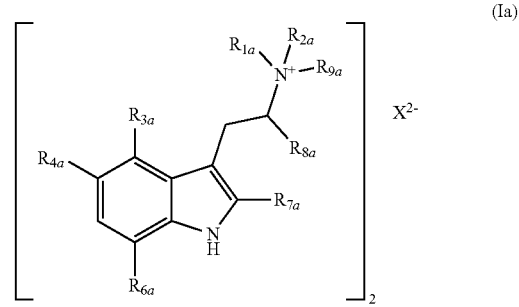

2 Claims, No Drawings

(56) References Cited

OTHER PUBLICATIONS

Dinis-Oliveira, R. J. (2017). Drug Metababolism Reviews, 49, 84-91.
Johnson, M. W. & Griffiths, R. R. (2017). Neurotherapeutics 14, 734-740.
C. Lenz, J. Wick and D. Hoffmeister, Journal of Natural Products, 2017, 80, 2835-2838.
A. M. Sherwood, et al., (2020). Journal of Natural Products, 83(2): 461-467.
Sheldrick, G. M. (2008). Acta Cryst. A64, 112-122.
Sheldrick, G. M. (2015). Acta Cryst. C71, 3-8.
Dolomanov, O. V., et al.,(2009). J. Appl. Cryst. 42, 339-341.
International Preliminary Report on Patentability in International Application No. PCT/US2021/062331 dated Jun. 13, 2023.
International Search Report and Written Opinion dated Apr. 7, 2022 issued in PCT Application No. PCT/US2021/062331.
Palamar et al., (2020) "A qualitative descriptive analysis of effects of psychedelic phenethylamines and tryptamines," Hum Psychopharmacol Clin Exp., 35,e2719.
The Big & Dan DY 4-AcO-DMT TH Read—Act Five (https://bluelight.org/xf/threads/the-big-dandy-4-aco-dmt-thread-act-five.742439/ (1 page of selected posts beginning Dec. 5, 2014) (Accessed Sep. 20, 2023).
Sard et al. (2005) "SAR of psilocybin analogs: Discovery of a selective 5-HT2C agonist." Bioorganic & Medicinal Chemistry Letters 15: 4555-4559.
Geiger et al. (2018), "Dark Classics in Chemical Neuroscience: Psilocybin", ACS Chem. Neurosci. 9(10), 2438-2447.

DIALKYL TRYPTAMINES AND THEIR THERAPEUTIC USES

CROSS-REFERENCE TO RELATED APPLICATIONS

This application claims priority to U.S. Provisional Application No. 63/123,203, filed on Dec. 9, 2020, and to U.S. Provisional Application No. 63/248,033, filed on Sep. 24, 2021, the disclosures of which are incorporated by reference.

TECHNICAL FIELD

This disclosure relates to tryptamines derivatives, compositions and pharmaceutical compositions containing them as well as their use in treating various diseases.

BACKGROUND OF THE INVENTION

Psilocybin is a breakthrough drug that has received FDA approval for therapeutic applications. Psilocybin is one of several naturally occurring psychoactive tryptamines found in "magic" mushrooms. When consumed by humans, psilocybin serves as a prodrug of psilocin. Psilocin is a potent serotonin 2a-agonist, which is responsible for its psychoactive properties (Dinis-Oliveira, 2017; Nichols, 2012). Upon digestion, psilocybin hydrolyses to generate psilocin. Psychoactive tryptamines like psilocin have garnered significant interest recently because of their potential for treating mood disorders, including depression, anxiety, addiction, and post-traumatic stress disorder (PTSD) (Johnson & Griffiths, 2017; Carhart-Harris & Goodwin, 2017). But psilocin is only one specific dialkytryptamine. And until this disclosure, there has been an unmet need for pure, well-characterized dialkytryptamines, including specific salts, solvates, and crystalline forms thereof.

SUMMARY OF THE INVENTION

The disclosure relates to a compound of formula (I):

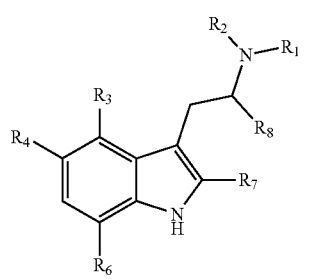

(I)

wherein
$R_1$ and $R_2$ are each independently a $C_1$-$C_6$ alkyl or a $C_2$-$C_6$ alkenyl;
one of $R_3$ and $R_4$ is hydrogen and the other of $R_3$ and $R_4$ is chosen from —$OR_5$, —$OC(O)R_5$, —$OC(O)OR_5$, or —$OSO_2R_5$;
$R_5$ is a $C_1$-$C_6$ alkyl or a substituted or unsubstituted aryl; and
$R_6$, $R_7$ and $R_8$ are each independently selected from hydrogen or a $C_1$—C alkyl;
or a pharmaceutically acceptable acid-addition salt thereof.

The disclosure also relates to a compound of formula (Ia):

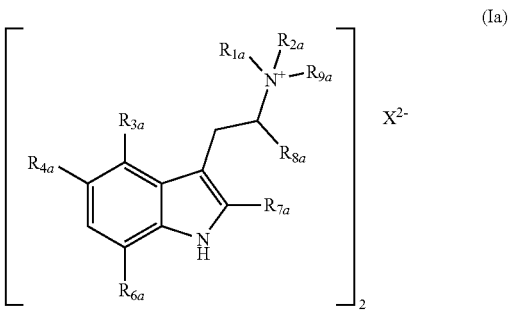

(Ia)

wherein
$R_{1a}$ and $R_{2a}$ are each independently a $C_1$-$C_6$ alkyl or a $C_1$-$C_6$ alkenyl; $R_{3a}$ and $R_{4a}$ are each independently selected from hydrogen, —$OR_{5a}$, —$OC(O)R_{5a}$, —$OC(O)OR_{5a}$, and —$OSO_2R_{5a}$;
$R_{5a}$ is a $C_1$-$C_6$ alkyl or a substituted or unsubstituted aryl;
$R_{6a}$, $R_{7a}$ and $R_{8a}$ are each independently selected from hydrogen or a $C_1$-$C_6$ alkyl;
$R_{9a}$ is hydrogen; and
$X^{2-}$ pharmaceutically-acceptable dianion.

The disclosure relates to compositions comprising, consisting essentially of, or consisting of a compound of formula (I) or formula (Ia) and an excipient. The disclosure also relates to pharmaceutical compositions comprising a therapeutically effective amount of a compound of formula (I) or formula (Ia) where the excipient is a pharmaceutically acceptable carrier. The disclosure further relates to a method of preventing or treating a psychological disorder comprising the step of administering to a subject in need thereof a therapeutically effective amount of a compound of formula (I) or formula (Ia) or of a pharmaceutical composition containing the compound.

The disclosure also relates to a composition comprising, consisting essentially of, or consisting of as a first active component: a compound of formula (I) or formula (Ia) of the disclosure; and as a second active component selected from (a) a serotonergic drug, (b) a purified psilocybin derivative, (c) one or two purified cannabinoids and (d) a purified terpene, (e) an adrenergic drug, (f) a dopaminergic drug, (g) a monoamine oxidase inhibitor, (h) a purified erinacine, and (i) a purified hericenone; and a pharmaceutically acceptable excipient.

The disclosure also relates to methods of preventing or treating inflammation and/or pain, preventing or treating a neurological disorder, modulating activity of a mitogen activating protein (MAP), modulating neurogenesis, or modulating neurite outgrowth comprising the step of administering to a subject in need thereof a therapeutically effective amount of a compound of formula (I) or formula (Ia), and to administering a pharmaceutical composition or a composition according to the disclosure.

The disclosure also relates to methods of preventing or treating sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

The disclosure also relates to methods of preventing or treating women's health disorders including, but not limited to, menstrual cramping, dysmenorrhea, post-hysterectomic pain, vaginal or vulvar vestibule mucosa disorder, vaginal atrophy, or vulvar vestibulitis.

DETAILED DESCRIPTION

Compounds of the Disclosure

This disclosure relates to tryptamine compounds of formula (I):

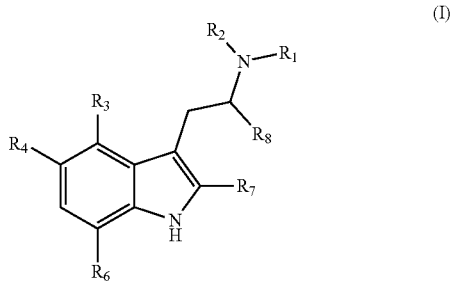

wherein
$R_1$ and $R_2$ are each independently a $C_1$-$C_6$ alkyl or a $C_2$-$C_6$ alkenyl;
one of $R_3$ and $R_4$ is hydrogen and the other of $R_3$ and $R_4$ is chosen from —$OR_5$, —$OC(O)R_5$, —$OC(O)OR_5$, or —$OSO_2R_5$;
$R_5$ is a $C_1$-$C_6$ alkyl or a substituted or unsubstituted aryl; and
$R_6$, $R_7$ and $R_8$ are each independently selected from hydrogen or a $C_1$-$C_6$ alkyl;
or a pharmaceutically acceptable acid-addition salt thereof.

In formula (I), $R_1$ and $R_2$ are each independently a $C_1$-$C_6$ alkyl or a $C_2$-$C_6$ alkenyl. $R_1$ and/or $R_2$ may be a straight chain or branched $C_1$-$C_6$ alkyl, for example a straight chain $C_1$-$C_6$ alkyl, or a straight chain or branched $C_2$-$C_6$ alkenyl, for example allyl, 2-butenyl, etc. In some embodiments, $R_1$ and/or $R_2$ may be a straight chain or branched $C_1$-$C_4$ alkyl, for example a straight chain $C_1$-$C_4$ alkyl, or a $C_2$-$C_4$ alkenyl. $R_1$ and/or $R_2$ may be selected from methyl, ethyl, n-propyl, isopropyl, cyclopropyl, n-butyl, isobutyl or tert-butyl. In other embodiments, $R_1$ and/or $R_2$ may be methyl, ethyl, propyl or isopropyl.

In formula (I), one of $R_3$ and $R_4$ is hydrogen and the other of $R_3$ and $R_4$ is chosen from —$OR_5$, —$OC(O)CH_2R_5$, —$OC(O)OR_5$, and —$OSO_2R_5$. When $R_3$ or $R_4$ are $C_1$-$C_6$ alkoxy group, or in some embodiments a $C_1$-$C_4$ alkoxy group, it may be a straight chain or branched $C_1$-$C_6$ alkoxy group or $C_1$-$C_4$ alkoxy group, for example a straight chain, and may be methoxy or ethoxy. $R_5$ is a straight chain or branched $C_1$-$C_6$ alkyl or a substituted or unsubstituted aryl. $R_5$ may be a straight chain or branched $C_1$-$C_4$ alkyl, for example a straight chain $C_1$-$C_4$ alkyl. In some embodiments, $R_5$ is selected from methyl, ethyl, n-propyl or n-butyl, and for example is methyl or ethyl. $R_5$ may also be a substituted or unsubstituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl and phenantherenyl. An aryl group may be substituted with one or more $C_1$-$C_4$ alkyl or perfluoralkyl groups, $C_1$-$C_4$ hydroxy-alkyl groups, hydroxyl groups, nitro groups or halo groups (e.g. F, Cl, I or Br). An aryl group may be ortho-, meta- and/or para-substituted, preferably para-substituted. When an aryl group is substituted with one or more straight chain or branched $C_1$-$C_4$ alkyl perfluoralkyl groups the group may be methyl, trifluromethyl, ethyl, n-propyl, isopropyl, n-butyl, isobutyl or tert-butyl or the group may be methyl, ethyl, isopropyl, or tert-butyl. When $R_3$ or $R_4$ is —$OR_5$, —$OC(O)R_5$, —$OC(O)OR_5$, or —$OSO_2R_5$, $R_5$ may be a methyl (except when $R_3$ is —$OC(O)R_5$, $R_5$ is not methyl), a tert-butyl, a phenyl, a benzyl, a para-halophenyl or a para-tolyl group.

$R_6$, $R_7$ and $R_8$ in formula (I) are each independently hydrogen or a $C_1$-$C_6$ alkyl, for example a straight chain or branched $C_1$-$C_6$ alkyl. In some embodiments, $R_6$, $R_7$ and $R_8$ are each independently selected hydrogen, methyl, ethyl, n-propyl, isopropyl, n-butyl, and isobutyl. In other embodiments, $R_6$, $R_7$ and $R_8$ are each independently hydrogen, methyl, or ethyl.

Pharmaceutically acceptable salts may be any acid (e.g. HX or $H_2X$) addition salts. The anion, $X^-$, may be any pharmaceutically acceptable anion, for example, $Cl^-$, $I^-$, $Br^-$, ascorbate, or hydrofumarate, and the like. Other pharmaceutically acceptable salts may be prepared by anion exchange techniques known in the art to exchange the iodide anion for a desired pharmaceutically acceptable anion. For example, the iodide anion may be exchanged using an anion exchange resin.

Exemplary compounds of formula (I) are those where one of $R_3$ and $R_4$ is hydrogen and the other $R_3$ and $R_4$ is —$OSO_2R_5$.

Other exemplary compounds of formula (I) are those with the proviso that when $R_3$ is hydrogen and $R_4$ is —$OSO_2R_5$, $R_1$ and $R_2$ are both ethyl, and $R_3$, $R_6$ and $R_7$ are all hydrogen, $R_5$ is not methyl, phenyl, or para-tolyl.

Other exemplary compounds of formula (I) are where $R_3$ is —$OC(O)R_5$ and $R_4$ is hydrogen, with the proviso that $R_5$ is not methyl when $R_1$ and $R_2$ are methyl and $R_6$, $R_7$, and $R_8$ are hydrogen.

Other exemplary compounds of formula (I) are where $R_3$ is —$OC(O)R_5$ and $R_4$ is hydrogen, with the proviso that $R_5$ is not methyl when one of $R_1$ and $R_2$ is methyl and the other of $R_1$ and $R_2$ is ethyl and $R_6$, $R_7$, and $R_8$ are hydrogen.

Other exemplary compounds of formula (I) are where $R_3$ is —$OC(O)R_5$ and $R_4$ is hydrogen, with the proviso that $R_5$ is not methyl when one of $R_1$ and $R_2$ is methyl and the other of $R_1$ and $R_2$ is allyl and $R_6$, $R_7$, and $R_8$ are hydrogen.

Other exemplary compounds of formula (I) are where $R_3$ is —$OC(O)R_5$ and $R_4$ is hydrogen, with the proviso that $R_5$ is not methyl when $R_1$ and $R_2$ are allyl and $R_6$, $R_7$, and $R_8$ are hydrogen.

Other exemplary compounds of formula (I) are where $R_3$ is —$OSO_2R_5$ and $R_4$ is hydrogen.

Other exemplary compounds of formula (I) are where one of $R_3$ and $R_4$ is hydrogen and the other $R_3$ and $R_4$ is —$OC(O)OR_5$.

Other exemplary compounds of formula (I) are where $R_3$ is hydrogen and $R_4$ is —$OC(O)R_5$, wherein $R_5$ is selected from substituted or unsubstituted aryl.

Other exemplary compounds of formula (I) are where $R_3$ is hydrogen and $R_4$ is —$OR_5$, with the proviso that $R_5$ is not methyl when $R_1$ and $R_2$ are propyl and $R_6$, $R_7$, and $R_8$ are hydrogen.

Other exemplary compounds of formula (I) are where $R_3$ is hydrogen and $R_4$ is —$OR_5$, with the proviso that $R_5$ is not methyl when $R_1$ and $R_2$ are allyl and $R_6$, $R_7$, and $R_8$ are hydrogen.

Other exemplary compounds of formula (I) are where $R_6$ is hydrogen.

Other exemplary compounds of formula (I) are where $R_7$ is hydrogen.

Other exemplary compounds of formula (I) are where $R_5$ is hydrogen.

Other exemplary compounds of formula (I) are where $R_5$ is a $C_1$-$C_6$ alkyl.

Other exemplary compounds of formula (I) are where $R_5$ is methyl.

Other exemplary compounds of formula (I) are where $R_5$ is a $C_2$-$C_6$ alkyl.

Other exemplary compounds of formula (I) are where $R_5$ is ethyl.

Other exemplary compounds of formula (I) are where $R_5$ is a $C_3$-$C_6$ alkyl.

Other exemplary compounds of formula (I) are where $R_5$ is propyl or isopropyl.

Other exemplary compounds of formula (I) are where $R_5$ is aryl.

Other exemplary compounds of formula (I) are where $R_5$ is phenyl.

Other exemplary compounds of formula (I) are where $R_1$ and $R_2$ are each independently selected from a $C_1$-$C_6$ alkyl.

Other exemplary compounds of formula (I) are where $R_1$ and $R_2$ are each independently selected from a $C_2$-$C_6$ alkyl.

Other exemplary compounds of formula (I) are where $R_1$ and $R_2$ are each independently selected from a $C_3$-$C_6$ alkyl.

Other exemplary compounds of formula (I) are where each of $R_1$ and $R_2$ are independently selected from methyl, ethyl, n-propyl, and isopropyl.

Other exemplary compounds of formula (I) are listed below:

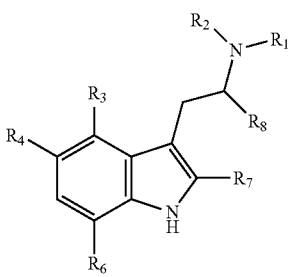

(I)

Compound 1: 4-butanoyloxy-N,N-di-n-propyltryptamine
Compound 2: 4-butanoyloxy-N,N-di-n-propyltryptammonium chloride
Compound 3: 4-propionoxy-N,N-dipropyltryptamine
Compound 4: 4-propionoxy-N,N-di-n-propyltryptammonium chloride
Compound 5: 4-(2-methylpropionoxy)-N,N-di-n-propyltryptamine
Compound 6: 4-(2-methylpropionoxy)-N,N-di-n-propyltryptammonium chloride
Compound 7: 4-benzoyloxy-N,N-di-n-propyltryptamine
Compound 8: 4-benzoyloxy-N,N-di-n-propyltryptammonium chloride
Compound 9: 4-(4-chlorobenzoyloxy)-N,N-di-n-propyltryptamine
Compound 10: 4-(4-chlorobenzoyloxy)-N,N-di-n-propyltryptammonium chloride
Compound 11: 4-(4-bromobenzoyloxy)-N,N-di-n-propyltryptamine
Compound 12: 4-(4-bromobenzoyloxy)-N,N-di-n-propyltryptammonium chloride
Compound 13: 4-(4-fluorobenzoyloxy)-N,N-di-n-propyltryptamine
Compound 14: 4-(4-fluorobenzoyloxy)-N,N-di-n-propyltryptammonium chloride
Compound 15: 4-(4-nitrobenzoyloxy)-N,N-di-n-propyltryptamine
Compound 16: 4-(4-nitrobenzoyloxy)-N,N-di-n-propyltryptammonium chloride
Compound 17: 4-p-toloyloxy-N,N-di-n-propyltryptamine
Compound 18: 4-p-toloyloxy-N,N-di-n-propyltryptammonium chloride
Compound 19: 4-pivaloyloxy-N,N-di-n-propyltryptamine
Compound 20: 4-pivaloyloxy-N,N-di-n-propyltryptammonium chloride
Compound 21: 4-(methylcarbanato)-N,N-di-n-propyltryptamine
Compound 22: 4-(methylcarbanato)-N,N-di-n-propyltryptammonium chloride
Compound 23: 4-(methylsulfonyloxy)-N,N-di-n-propyltryptamine
Compound 24: 4-(methylsulfonyloxy)-N,N-di-n-propyltryptammonium chloride
Compound 25: 4-(ethylsulfonyloxy)-N,N-di-n-propyltryptamine
Compound 26: 4-(ethylsulfonyloxy)-N,N-di-n-propyltryptammonium chloride
Compound 27: 4-(propylsulfonyloxy)-N,N-di-n-propyltryptamine
Compound 28: 4-(propylsulfonyloxy)-N,N-di-n-propyltryptammonium chloride
Compound 29: 4-(isopropylsulfonyloxy)-N,N-di-n-propyltryptammonium chloride
Compound 30: 4-(phenylsulfonyloxy)-N,N-di-n-propyltryptamine
Compound 31: 4-(phenylsulfonyloxy)-N,N-di-n-propyltryptammonium chloride
Compound 32: 4-(p-tolylsulfonyloxy)-N,N-di-n-propyltryptamine
Compound 33: 4-(p-tolylsulfonyloxy)-N,N-di-n-propyltryptammonium chloride
Compound 34: 4-[4-(trifluoromethyl)phenylsulfonyloxy]-N,N-di-n-propyltryptamine
Compound 35: 4-[4-(trifluoromethyl)phenylsulfonyloxy]-N,N-di-n-propyltryptammonium chloride
Compound 36: 4-[(4-nitrophenyl)sulfonyloxy]-N,N-di-n-propyltryptamine
Compound 37: 4-[(4-nitrophenyl)sulfonyloxy]-N,N-di-n-propyltryptammonium chloride
Compound 38: 4-[(4-chlorophenyl)sulfonyloxy]-N,N-di-n-propyltryptamine
Compound 39: 4-[(4-chlorophenyl)sulfonyloxy]-N,N-di-n-propyltryptammonium chloride
Compound 40: 4-[(4-bromophenyl)sulfonyloxy]-N,N-di-n-propyltryptamine
Compound 41: 4-[(4-bromophenyl)sulfonyloxy]-N,N-di-n-propyltryptammonium chloride
Compound 42: 4-[(4-fluorophenyl)sulfonyloxy]-N,N-di-n-propyltryptamine
Compound 43: 4-[(4-fluorophenyl)sulfonyloxy]-N,N-di-n-propyltryptammonium chloride
Compound 44: 5-Methoxy-N,N-dimethyltryptamine Compound 45: 5-Methoxy-N-methyl, N-isopropyltryptamine Compound 46: 5-Methoxy-N-methyl, N-ethyltryptamine Compound 47: Bis[5-Methoxy-N-methyl, N-ethyltryptammonium] fumarate Compound 48: 5-Methoxy-N,N-di-isopropyltryptamine Compound 49: 2-Methyl, 5-methoxy-N,N-dimethyltryptamine Compound 50: Bis[2-Methyl, 5-methoxy-N,N-dimethyltryptammonium] fumarate Compound 51: 2-Methyl, 5-methoxy-N,N-diallyltryptamine Compound 52: Bis[2-Methyl, 5-methoxy-N,N-diallyltryptammonium] fumarate Compound 53: 4-acetoxy-N,N-dimethyltryptamine Compound 54: 4-acetoxy-N,N-diallyltryptamine Compound 55: 4-acetoxy-N-ethyl-N-methyltryptamine Compound 56: 4-acetoxy-N-allyl-N-methyltryptamine Compound 57: 4-acetoxy-N,N-di-n-ethyltryptamine Compound 58: 4-acetoxy-N,N-dipropyltryptamine Compound 59: 4-acetoxy-N,N-diisopropyltryptamine Compound 60: 4-acetoxy-N-methyl-N-propyltryptamine Compound 61: 4-acetoxy-N-methyl-N-isopropyltryptamine Compound 62: Bis[4-acetoxy-N,N-dimethyltryptammonium] fumarate Compound 63: Bis[4-acetoxy-N,N-diallyltryptammonium] fumarate Compound 64: 4-acetoxy-N-ethyl-N-methyltryptammonium hydrofumarate Compound 65: 4-acetoxy-N-allyl-N-methyltryptammonium hydrofumarate Compound 66: 4-acetoxy-N,N-dimethyltryptammonium hydrofumarate Compound 67: 4-acetoxy-N,N-dipropyltryptammonium chloride Compound 68: 4-acetoxy-N-ethyl-N-propyltryptamine Compound 69: Bis[4-acetoxy-N-ethyl-N-methyltryptammonium] fumarate Compound 70: Bis[4-acetoxy-N-methyl-N-propyltryptammonium] fumarate Compound 71: Bis[4-acetoxy-N-methyl-N-isopropyltryptammonium] fumarate Compound 72: Bis[4-acetoxy-N,N-di-n-ethyltryptammonium] fumarate Compound 73: Bis[4-acetoxy-N-ethyl-N-propyltryptammonium] fumarate Compound 74: Bis[4-acetoxy-N,N-dipropyltryptammonium] fumarate Compound 75: 4-acetoxy-N,N-diisopropyltryptammonium acetate Compound 76: 4-acetoxy-N,N-dimethyltryptammonium chloride Compound 77: 4-acetoxy-N-methyl-N-isopropyltryptammonium chloride Compound 78: 4-acetoxy-N,N-di-n-ethyltryptammonium chloride Compound 79: 4-acetoxy-N,N-diisopropyltryptammonium chloride This disclosure also relates to purified tryptamine compounds of formula (I):

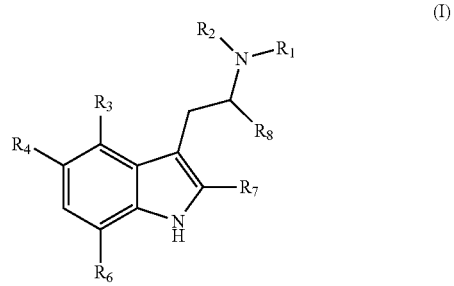

(I)

wherein $R_1$ and $R_2$ are each independently a $C_1$-$C_6$ alkyl or a $C_2$-$C_6$ alkenyl;

one of $R_3$ and $R_4$ is hydrogen and the other of $R_3$ and $R_4$ is chosen from —$OR_5$, —$OC(O)R_5$, —$OC(O)OR_5$, or —$OSO_2R_5$;

$R_5$ is a $C_1$-$C_6$ alkyl or a substituted or unsubstituted aryl; and $R_6$, $R_7$ and $R_5$ are each independently selected from hydrogen or a $C_1$-$C_6$ alkyl;

or a pharmaceutically acceptable acid-addition salt thereof;

wherein the purity of the tryptamine compound of formula (I) is greater than 95%, greater than 98%, greater than 99%, or greater than 99.9%.

This disclosure also relates to tryptammonium compounds of formula (Ia):

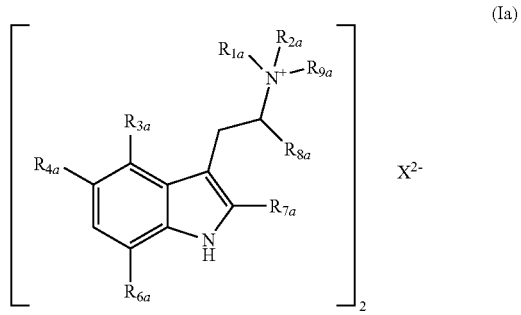

(Ia)

wherein $R_{1a}$ and $R_{2a}$ are each independently a $C_1$-$C_6$ alkyl or a $C_2$-$C_6$ alkenyl;

$R_{3a}$ and $R_{4a}$ are each independently selected from hydrogen, —$OR_{5a}$, —$OC(O)R_{5a}$, —$OC(O)OR_{5a}$, and —$OSO_2R_{5a}$;

$R_{5a}$ is a $C_1$-$C_6$ alkyl or a substituted or unsubstituted aryl;

$R_{6a}$, $R_{7a}$ and $R_{5a}$ are each independently selected from hydrogen or a $C_1$-$C_6$ alkyl;

$R_{9a}$ is hydrogen; and $X^{2-}$ pharmaceutically-acceptable dianion.

In formula (Ia), $R_{1a}$ and $R_{2a}$ are each independently a $C_1$-$C_6$ alkyl or a $C_2$-$C_6$ alkenyl. $R_{1a}$ and/or $R_{2a}$ may be a straight chain or branched $C_1$-$C_6$ alkyl, for example a straight chain $C_1$-$C_6$ alkyl, or a straight chain or branched $C_2$-$C_6$ alkenyl, for example allyl, 2-butenyl, etc. In some embodiments, $R_{1a}$ and/or $R_{2a}$ may be a straight chain or branched $C_1$-$C_4$ alkyl, for example a straight chain $C_1$-$C_4$ alkyl, or a $C_2$-$C_4$ alkenyl. $R_{1a}$ and/or $R_{2a}$ may be selected from methyl, ethyl, n-propyl, isopropyl, cyclopropyl, n-butyl, isobutyl or tert-butyl. In other embodiments, $R_{1a}$ and/or $R_{2a}$ may be methyl, ethyl, propyl or isopropyl.

In formula (Ia), one of $R_{3a}$ and $R_{4a}$ is hydrogen and the other of $R_{3a}$ and $R_{4a}$ is chosen from —$OR_{5a}$, —$OC(O)CH_2R_{5a}$, —$OC(O)OR_{5a}$, and —$OSO_2R_{5a}$. When $R_{3a}$ or $R_{4a}$ are $C_1$-$C_6$ alkoxy group, or in some embodiments a $C_1$-$C_4$ alkoxy group, it may be a straight chain or branched $C_1$-$C_6$ alkoxy group or $C_1$-$C_4$ alkoxy group, for example a straight chain, and may be methoxy or ethoxy. $R_{5a}$ is a straight chain or branched $C_1$-$C_6$ alkyl or a substituted or unsubstituted aryl. $R_{5a}$ may be a straight chain or branched $C_1$-$C_4$ alkyl, for example a straight chain $C_1$-$C_4$ alkyl. In some embodiments, $R_{5a}$ is selected from methyl, ethyl, n-propyl or n-butyl, and for example is methyl or ethyl. $R_{5a}$ may also be a substituted or unsubstituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl and phenantherenyl. An aryl group may be substituted with one or more $C_1$-$C_4$ alkyl or perfluoralkyl groups, $C_1$-$C_4$ hydroxyalkyl groups, hydroxyl groups, nitro groups or halo groups (e.g. F, Cl, I or Br). An aryl group may be ortho-, meta- and/or para-substituted, preferably para-substituted. When an aryl group is substituted with one or more straight chain or branched $C_1$-$C_4$ alkyl perfluoralkyl groups the group may be methyl, trifluromethyl, ethyl, n-propyl, isopropyl, n-butyl, isobutyl or tert-butyl or the group may be methyl, ethyl, isopropyl, or tert-butyl. When $R_{3a}$ or $R_{4a}$ is —$OR_{5a}$, —$OC(O)R_{5a}$, —$OC(O)OR_{5a}$, or —$OSO_2R_{5a}$, $R_{5a}$ may be a methyl (except when $R_{3a}$ is —$OC(O)R_{5a}$, $R_{5a}$ is not methyl), a tert-butyl, a phenyl, a benzyl, a para-halophenyl or a para-tolyl group.

$R_{6a}$, $R_{7a}$ and $R_{8a}$ in formula (Ia) are each independently hydrogen or a $C_1$-$C_6$ alkyl, for example a straight chain or branched $C_1$-$C_6$ alkyl. In some embodiments, $R_{6a}$, $R_{7a}$ and $R_{8a}$ are each independently selected hydrogen, methyl, ethyl, n-propyl, isopropyl, n-butyl, and isobutyl. In other embodiments, $R_{6a}$, $R_{7a}$ and $R_{8a}$ are each independently hydrogen, methyl, or ethyl.

In formula (Ia) the anion, $X^{2-}$, may be any pharmaceutically acceptable dianion, e.g., fumarate, maleate, malonate, succinate, tartarate, or oxalate, and the like. Other pharmaceutically acceptable salts may be prepared by anion exchange techniques known in the art to exchange the iodide anion for a desired pharmaceutically acceptable anion. For example, the iodide anion may be exchanged using an anion exchange resin.

Exemplary compounds of formula (Ia) are those where one of $R_3$ and $R_4$ is hydrogen and the other of $R_3$ and $R_4$ is chosen from —$OR_{5a}$, —$OC(O)R_{5a}$, —$OC(O)OR_{5a}$, and —$OSO_2R_{5a}$.

Other exemplary compounds of formula (Ia) are those where one of $R_{3a}$ and $R_{4a}$ is hydrogen and the other $R_{3a}$ and $R_{4a}$ is —$OSO_2R_{5a}$.

Other exemplary compounds of formula (Ia) are those with the proviso that when $R_{3a}$ is hydrogen and $R_{4a}$ is —$OSO_2R_{5a}$, $R_{1a}$ and $R_{2a}$ are both ethyl, and $R_{3a}$, $R_{6a}$ and $R_{7a}$ are all hydrogen, $R_{5a}$ is not methyl, phenyl, or para-tolyl.

Other exemplary compounds of formula (Ia) are where $R_{3a}$ is —$OC(O)R_{5a}$ and $R_{4a}$ is hydrogen, with the proviso that $R_{5a}$ is not methyl when $R_{1a}$ and $R_{2a}$ are methyl and $R_{6a}$, $R_{7a}$, $R_{8a}$, and $R_{9a}$ are hydrogen.

Other exemplary compounds of formula (Ia) are where $R_{3a}$ is —$OC(O)R_{5a}$ and $R_{4a}$ is hydrogen, with the proviso that $R_{5a}$ is not methyl when one of $R_{1a}$ and $R_{2a}$ is ethyl and the other of $R_{1a}$ and $R_{2a}$ is propyl and $R_{6a}$, $R_{7a}$, $R_{8a}$, and $R_{9a}$ are hydrogen.

Other exemplary compounds of formula (Ia) are those where $R_{3a}$ is —$OSO_2R_{5a}$ and $R_{4a}$ is hydrogen.

Other exemplary compounds of formula (Ia) are those where one of $R_{3a}$ and $R_{4a}$ is hydrogen and the other $R_{3a}$ and $R_{4a}$ is —$OC(O)OR_{5a}$.

Other exemplary compounds of formula (Ia) are those where $R_{3a}$ is hydrogen and $R_{4a}$ is —$OC(O)R_{5a}$, wherein $R_{5a}$ is selected from substituted or unsubstituted aryl.

Other exemplary compounds of formula (Ia) are where $R_{3a}$ is hydrogen and $R_{4a}$ is —$OR_{5a}$, with the proviso that $R_{5a}$ is not methyl when $R_{1a}$ and $R_{2a}$ are propyl and $R_{6a}$, $R_{7a}$, $R_{8a}$, and $R_{9a}$ are hydrogen.

Other exemplary compounds of formula (Ia) are where $R_{3a}$ is hydrogen and $R_{4a}$ is —$OR_{5a}$, with the proviso that $R_{5a}$ is not methyl when $R_{1a}$ and $R_{2a}$ are allyl and $R_{6a}$, $R_{7a}$, $R_{8a}$, and $R_{9a}$ are hydrogen.

Other exemplary compounds of formula (Ia) are those where $R_{6a}$ is hydrogen.

Other exemplary compounds of formula (Ia) are those where $R_{7a}$ is hydrogen.

Other exemplary compounds of formula (Ia) are those where $R_{8a}$ is hydrogen.

Other exemplary compounds of formula (Ia) are those where $R_{5a}$ is a $C_1$-$C_6$ alkyl.

Other exemplary compounds of formula (Ia) are those where $R_{5a}$ is methyl.

Other exemplary compounds of formula (Ia) are those where $R_{5a}$ is a $C_2$-$C_6$ alkyl.

Other exemplary compounds of formula (Ia) are those where $R_{5a}$ is ethyl.

Other exemplary compounds of formula (Ia) are those where $R_{5a}$ is a $C_3$-$C_6$ alkyl.

Other exemplary compounds of formula (Ia) are those where $R_{5a}$ is propyl or isopropyl.

Other exemplary compounds of formula (Ia) are those where $R_{5a}$ is aryl.

Other exemplary compounds of formula (Ia) are those where $R_{5a}$ is phenyl.

Other exemplary compounds of formula (Ia) are those where $R_{1a}$ and $R_{2a}$ are each independently selected from a $C_1$-$C_6$ alkyl.

Other exemplary compounds of formula (Ia) are those where $R_{1a}$ and $R_{2a}$ are each independently selected from a $C_2$-$C_6$ alkyl.

Other exemplary compounds of formula (Ia) are those where $R_{1a}$ and $R_{2a}$ are each independently selected from a $C_3$-$C_6$ alkyl.

Other exemplary compounds of formula (Ia) are those where each of $R_{1a}$ and $R_{2a}$ are independently selected from methyl, ethyl, n-propyl, and isopropyl.

Other exemplary compounds of formula (Ia) are those where $X^{2-}$ is selected from fumarate, malonate, succinate, tartarate, oxalate, and maleate.

This disclosure also relates to purified tryptammonium compounds of formula (Ia):

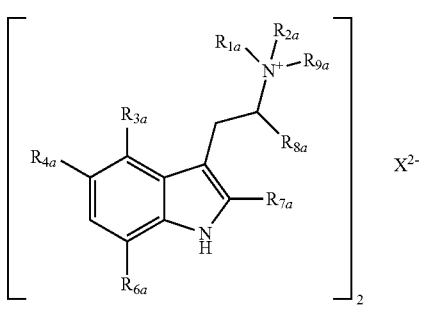

wherein
- $R_{1a}$ and $R_{2a}$ are each independently a $C_1$-$C_6$ alkyl or a $C_2$-$C_6$ alkenyl;
- $R_{3a}$ and $R_{4a}$ are each independently selected from hydrogen, $-OR_{5a}$, $-OC(O)R_{5a}$, $-OC(O)OR_{5a}$, and $-OSO_2R_{5a}$;
- $R_{5a}$ is a $C_1$-$C_6$ alkyl or a substituted or unsubstituted aryl;
- $R_{6a}$, $R_{7a}$ and $R_{8a}$ are each independently selected from hydrogen or a $C_1$-$C_6$ alkyl;
- $R_{9a}$ is hydrogen; and
- $X^{2-}$ pharmaceutically-acceptable dianion;
- wherein the purity of the tryptammonium compound of formula (Ia) is greater than 95%, greater than 98%, greater than 99%, or greater than 99.9%.

A compound of formula (I) or formula (Ia) may be prepared by a variety of methods known in the organic synthesis art. As shown in the examples below, compounds of formula (I) or formula (Ia) may be prepared by reacting the corresponding indol-4-ol or indol-5-ol compound with an appropriate esterifying agent (e.g., an acid chloride) in the presence of a base (e.g., an amine base). Ether compounds of formula (I) or formula (Ia) made be from the corresponding hydroxy compound or starting material using means known in the art, such as reaction with an akyl halide or other alkylating agent. See, e.g., Protective Groups in Organic Synthesis, https://www.wiley.com/en-us/Greene %27s+Protective+Groups+in+Organic+Synthesis %2C+5th+Edition-p-9781118057483.

In one embodiment, the compound of formula (I) or (Ia) serves as a prodrug of a biologically active compound in a manner akin to the prodrug psilocybin's hydrolysis into psilocin, its known active. In one embodiment, the compounds of this disclosure provide advantages in their rates of conversion (e.g., hydrolysis into the active compound). In one embodiment, the rate of hydrolysis is increased relative to psilocybin. In another embodiment, the rate of hydrolysis is decreased relative to psilocybin. The comparative rates of hydrolysis can be measured by dissolving a compound in water and measuring either the disappearance of that compound and/or the appearance of the product of the hydrolysis of that compound. For example, in the case of psilocybin: psilocybin can be dissolved in water; and its conversion into psilocin can be measured by NMR (or similar spectroscopic techniques) by following the amount of psilocybin relative to an internal standard and/or the amount of psilocin relative to an internal standard. Comparative studies can be conducted for similar molecules, holding the pH, concentration, and temperature constant across each experiment.

In one embodiment, the compound for formula (I) or (Ia) hydrolyzes into an active (e.g., the corresponding indol-4-ol or indol-5-ol compound) faster than psilocybin hydrolyzes into psilocin. In one example, the compound of formula (I) or (Ia) hydrolyzes between 10% to 100% faster. In one example, the compound of formula (I) or (Ia) hydrolyzes between 30% to 80% faster. In one example, the compound of formula (I) or (Ia) hydrolyzes between 40% to 60% faster. In one example, the compound of formula (I) or (Ia) hydrolyzes more than 100% faster. In one example, the compound of formula (I) or (Ia) hydrolyzes between 100%-1000% faster. In one example, the compound of formula (I) or (Ia) hydrolyzes between 3000%-5,000% faster. In one example, the compound of formula (I) or (Ia) hydrolyzes between 1000%-10,000% faster.

In one embodiment, the compound for formula (I) or (Ia) hydrolyzes into an active (e.g., the corresponding indol-4-ol or indol-5-ol compound) slower than psilocybin hydrolyzes into psilocin. In one embodiment, the compound of formula (I) or (Ia) hydrolyzes at less than 80% of the rate that psilocybin hydrolyzes into psilocin. In one embodiment, the compound of formula (I) or (Ia) hydrolyzes at less than 60% of the rate that psilocybin hydrolyzes into psilocin. In one embodiment, the compound of formula (I) or (Ia) hydrolyzes at less than 40% of the rate that psilocybin hydrolyzes into psilocin. In one embodiment, the compound of formula (I) or (Ia) hydrolyzes at less than 10% of the rate that psilocybin hydrolyzes into psilocin. In one embodiment, the compound of formula (I) or (Ia) hydrolyzes at less than 5% of the rate that psilocybin hydrolyzes into psilocin.

The above-described differences in the rates of hydrolysis offer advantages vis-à-vis psilocybin's conversion into psilocin. In one embodiment, compounds of formula (I) or (Ia) provide increased bioavailability (compared to psilocybin/psilocin) of their corresponding indol-4-ol or indol-5-ol compounds, which can be determined and demonstrated by comparing the ED50 values in murine Head Twitch Response experiments. One example of a comparison showing a compound of formula (I) or (Ia) that hydrolyzes into an active (e.g., the corresponding indol-4-ol or indol-5-ol compound) faster than psilocybin hydrolyzes into psilocin is shown below in Table 1 where CT-421X is a compound for formula (I) and CT-421Y is a compound of formula (Ia):

TABLE 1

|          | HTR ED50 (uM/kg)        | Hydrolysis rate |
|----------|-------------------------|-----------------|
| Psilocin | 0.54                    | n/a             |
| Psilocybin | 1.02                  | 0.03            |
| CT-421X  | 0.58                    | 1               |
| CT-421Y  | 0.2-0.6 (preliminary)   | 1               |

One example of a comparison showing a compound of formula (I) or (Ia) that hydrolyzes into an active (e.g., the corresponding indol-4-ol or indol-5-ol compound) slower than psilocybin hydrolyzes into psilocin is shown below in Table 2:

TABLE 2

| Compound ID | $k_{obs}$ (s$^{-1}$) × 10$^{-6}$ | Apparent $t_{1/2}$ |
|-------------|----------------------------------|--------------------|
| Psilocybin  | <1                               | <1 year            |
| CT-4213     | <1                               | >15 years          |

Methods of Treatment and Therapeutic Uses

Compounds of formula (I) or formula (Ia) according to the disclosure, crystalline forms thereof, and the methods and the compositions (e.g., pharmaceutical compositions) are used to regulate the activity of a neurotransmitter receptor by administering a therapeutically effective dose of compounds of formula (I) or formula (Ia) according to the disclosure, and the methods and the compositions (e.g., pharmaceutical compositions) are used to treat inflammation and/or pain by administering a therapeutically effective dose of compounds of formula (I) or formula (Ia) according to the disclosure.

Methods of the disclosure also related to the administration of a therapeutically effective amount of compounds of formula (I) or formula (Ia) according to the disclosure to prevent or treat a disease or condition, such as those discussed below for a subject in need of treatment. Compounds of formula (I) or formula (Ia) according to the disclosure may be administered neat or as a composition comprising compounds of formula (I) or formula (Ia) according to the disclosure as discussed below.

Compounds of formula (I) or formula (Ia) according to the disclosure may be used to prevent and/or treat a psychological disorder. The disclosure provides a method for preventing and/or treating a psychological disorder by administering to a subject in need thereof a therapeutically effective amount of compounds of formula (I) or formula (Ia) according to the disclosure, including the exemplary embodiments discussed herein. The psychological disorder may be chosen from depression, psychotic disorder, schizophrenia, schizophreniform disorder (acute schizophrenic episode); schizoaffective disorder; bipolar I disorder (mania, manic disorder, manic-depressive psychosis); bipolar 11 disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome, post-traumatic stress disorder (PTSD), premenstrual dysphoric disorder (PMDD), and premenstrual syndrome (PMS).

Compounds of formula (I) or formula (Ia) according to the disclosure may be used to prevent and/or treat a brain disorder. The disclosure provides a method for preventing and/or treating a brain disorder (e.g., Huntington's disease, Alzheimer's disease, dementia, and Parkinson's disease) by administering to a subject in need thereof a therapeutically effective amount of compounds of formula (I) or formula (Ia) according to the disclosure, including the exemplary embodiments discussed above.

Compounds of formula (I) or formula (Ia) according to the disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of compounds of formula (I) or formula (Ia) according to the disclosure, including the exemplary embodiments discussed above.

Compounds of formula (I) or formula (Ia) according to the disclosure may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of compounds of formula (I) or formula (Ia) according to the disclosure, including the exemplary embodiments discussed herein. Generally speaking, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e., mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

Compounds of formula (I) or formula (Ia) according to the disclosure may be used to modulate activity of a mitogen activating protein (MAP), comprising administering a composition of the disclosure. In one embodiment, the mitogen activating protein (MAP) comprises a MAP kinase (MAPk). MAPKs provide a wide-ranging signaling cascade that allow cells to quickly respond to biotic and abiotic stimuli. Exemplary MAPKs include, but are not limited to, Tropomyosin Receptor Kinase A (TrkA), P38-alpha, Janus Kinase 1 (JAK1), and c-Jun N-Terminal Kinase 3 (JNK3). TrkA is a high affinity catalytic receptor of nerve growth factor (NGF) protein. TrkA regulates NGF response, influencing neuronal differentiation and outgrowth as well as programmed cell death, p38-alpha is involved with the regulation of pro-inflammatory cytokines, including TNF-α. In the central nervous system, p38-alpha regulates neuronal death and neurite degeneration, and it is a common target of Alzheimer's disease therapies. JAK1 influences cytokine signaling, including IL-2, IL-4, IFN-alpha/beta, IFN-γ, and IL-10, and it is implicated in brain aging. JNK3 is neuronal specific protein isoform of the JNKs. It is involved with the regulation of apoptosis. JNK3 also plays a role in modulating the response of cytokines, growth factors, and oxidative stress.

As used herein, the term "modulating activity of a mitogen activating protein" refers to changing, manipulating, and/or adjusting the activity of a mitogen activating protein. In one embodiment, modulating the activity of a MAP, such as a MAPK, can influence neural health, neurogenesis, neural growth and differentiation, and neurodegenerative diseases.

Compounds of formula (I) or formula (Ia) according to the disclosure may be used to modulate neurogenesis, comprising administering a composition of the disclosure. As used herein, the term "modulating neurite outgrowth" refers to changing, manipulating, and/or adjusting the growth and development of neural projections, or "neurites." In one embodiment, neurogenesis comprises modulating the growth of new neurites, the number of neurites per neuron, and/or neurite length. In one embodiment, modulating neurite outgrowth comprises increasing and/or enhancing the rate and/or length at which neurites develop.

Compounds of formula (I) or formula (Ia) according to the disclosure may be used to modulate neurite outgrowth, comprising administering a composition of the disclosure. As used herein, the term "modulating neurogenesis" refers to changing, manipulating, and/or adjusting the growth and development of neural tissue. In one embodiment, neurogenesis comprises adult neurogenesis, in which new neural stem cells are generated from neural stem cells in an adult animal. In one embodiment, modulating neurogenesis comprises increasing and/or enhancing the rate at which new neural tissue is developed.

The disclosure also relates to methods of preventing or treating sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

The disclosure also relates to methods of preventing or treating women's health disorders including, but not limited to, menstrual cramping, dysmenorrhea, post-hysterectomic pain, vaginal or vulvar vestibule mucosa disorder, vaginal atrophy, or vulvar vestibulitis.

Compositions

The disclosure also relates to compositions comprising an effective amount of a compound of formula (I) or formula (Ia) according to the disclosure (dialkyl tryptamine compounds of the disclosure), including its exemplary embodiments discussed above, and an excipient (e.g., a pharmaceutically-acceptable excipient). In another embodiment, the disclosure also relates to pharmaceutical compositions comprising a therapeutically effective amount of dialkyl tryptamine compounds of the disclosure, including their exemplary embodiments discussed above, and a pharmaceutically acceptable excipient (also known as a pharmaceutically acceptable carrier). As discussed above, a dialkyl tryptamine compound of the disclosure may be, for example, therapeutically useful to prevent and/or treat the psychological disorders, brain disorders, pain, and inflammation as well as the other disorders described herein.

A composition or a pharmaceutical composition of the disclosure may be in any form which contains a dialkyl tryptamine compound of the disclosure. The composition may be, for example, a tablet, capsule, liquid suspension, injectable, topical, or transdermal. The compositions generally contain, for example, about 1% to about 99% by weight of a dialkyl tryptamine compound of the disclosure and, for example, 99% to 1% by weight of at least one suitable pharmaceutically acceptable excipient. In one embodiment, the composition may be between about 5% and about 75% by weight of a dialkyl tryptamine compound of the disclosure, with the rest being at least one suitable pharmaceutically acceptable excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, a dialkyl tryptamine compound of the disclosure may be used as the "first purified psilocybin derivative" in the compositions described in US 2018/0221396 A1 and US 2019/0142851 A1. Accordingly, this disclosure provides a composition comprising: a first component comprising at least one dialkyl tryptamine compound of the disclosure; at least one second component selected from at least one of (a) a serotonergic drug, (b) a purified psilocybin derivative, (c) a purified cannabinoid or (d) a purified terpene; and at least one pharmaceutically-acceptable excipient or at least one other adjuvant. Such a composition may be a pharmaceutical composition wherein the components are present individually in therapeutically effective amounts or by combination in a therapeutically effective amount to treat a disease, disorder, or condition as described herein.

When used in such compositions as a first component comprising at least one dialkyl tryptamine compound of the disclosure with a second component selected from at least one of (a) a serotonergic drug, (b) a purified psilocybin derivative, (c) a purified cannabinoid, or (d) a purified terpene, the compositions represent particular embodiments of the disclosure. Compositions having as a first component at least one dialkyl tryptamine compound of the disclosure with a second component selected from at least one of (e) an adrenergic drug, (f) a dopaminergic drug, (g) a monoamine oxidase inhibitor, (h) a purified erinacine, or (i) a purified hericenone, also represent additional particular embodiments of the disclosure represented by the compositions having the dialkyl tryptamine compound of the disclosure. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments, incorporated here by reference. Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed exemplary embodiments. Exemplary cannabinoids include but are not limited to the cannabinoids described in paragraphs [0111]-[0159] of US 2018/0221396 A1 and [0112]-[0160] US 2019/0142851 A1 as well as the disclosed exemplary embodiments. Exemplary terpenes include but are not limited to the terpenes described in paragraphs [0160]-[0238] of US 2018/0221396 A1 and [0161]-[0300] US 2019/0142851 A1 as well as the disclosed exemplary embodiments.

A pharmaceutical formulation of the disclosure may comprise, consist essentially of, or consist of (a) at least one dialkyl tryptamine compound of the disclosure and (b) at least one second active compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and (c) a pharmaceutically acceptable excipient. In some embodiments, the dialkyl tryptamine compound(s) of the disclosure and the second active compound(s) are each present in a therapeutically effective amount using a purposefully engineered and unnaturally occurring molar ratios. Exemplary molar ratios of the dialkyl tryptamine compounds of the disclosure to the second active compound in a composition of the disclosure include but are not limited to from about 0.1:100 to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition containing a dialkyl tryptamine compound of the disclosure and a serotonergic drug, a purified psilocybin derivative, a purified cannabinoid, or a purified terpene, each present in a therapeutically effective amount using a purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. The disclosures of US 2018/0221396 A1 and US 2019/0142851 A1 are incorporated herein by reference. According to this disclosure composition containing a dialkyl tryptamine compound of the disclosure may be used in place of a "purified psilocybin derivative" in the compositions described in US 2018/0221396 A1 and US 2019/0142851 A1. Accordingly, the disclosure provides a pharmaceutical formulation comprising as (a) at least one dialkyl tryptamine compound of the disclosure and at least one second component selected from (b) a purified psilocybin derivative, (c) a purified cannabinoid or (d) a purified terpene; and at least one pharmaceutically-acceptable excipient or at least one other adjuvant, as described herein. Such a composition may be a pharmaceutical composition wherein the components are present individually in therapeutic effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments, incorporated here by reference. Some exemplary serotonergic drugs include SSRIs and SNRIs. Some examples of specific serotonergic drugs include the following molecules, including any salts, solvates, or polymorphs thereof: 6-Allyl-N,N-diethyl-NL, N,N-Dibutyl-T, N,N-Diethyl-T, N,N-Diisopropyl-T, 5-Methyoxy-alpha-methyl-T, N,N-Dimethyl-T, 2, alpha-Dimethyl-T, alpha, N-Dimethyl-T, N,N-Dipropyl-T, N-Ethyl-N-isopropyl-T, alpha-Ethyl-T, 6,N,N-Triethyl-NL, 3,4-Dihydro-7-methoxy-1-methyl-C, 7-Methyoxy-1-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N, N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T Ibogaine, N,N-Diethyl-L, N-Butyl-N-methyl-T, N,N-Diisopropyl-4,5-methylenedioxy-T, N,N-Diisopropyl-5,6-methylenedioxy-T, N,N-Dimethyl-4,5-methylenedioxy-T, N,N-Dimethyl-5,6-methylenedioxy-T, N-Isopropyl-N-methyl-4,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5-methoxy-T, 5-Methoxy-N,N-dimethyl-T, N-Isopropyl-4-methoxy-N-methyl-T, N-Isopropyl-5-methoxy-N-methyl-T, 5,6-Dimethoxy-N-isopropyl-N-methyl-T, 5-Methoxy-N-methyl-T, 5-Methoxy-N,N-tetramethylene-T, 6-Methoxy-1-methyl-1,2,3,4-tetrahydro-C, 5-Methoxy-2,N,N-trimethyl-T, N,N-Dimethyl-5-methylthio-T, N-Isopropyl-N-methyl-T, alpha-Methyl-T, N-Ethyl-T, N-Methyl-T, 6-Propyl-N L, N,N-Tetramethylene-T, Tryptamine, and 7-Methoxy-1-methyl-1,2,3,4-tetrahydro-C, alpha,N-Dimethyl-5-methoxy-T. For additional information regarding these compounds see Shulgin, A. T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In an exemplary embodiment, the serotonergic drug is 3,4-methylenedioxymethamphetamine.

Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed exemplary embodiments, incorporated here by reference. In one embodiment, the compositions disclosed herein comprise one or more purified psilocybin derivatives chosen from: [3-(2-Dimethylaminoethyl)-1H-indol-4-yl] dihydrogen phosphate, 4-hydroxytryptamine, 4-hydroxy-N, N-dimethyltryptamine, [3-(2-methylaminoethyl)-1H-indol-4-yl]dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N,N,N-trimethyltryptamine.

Exemplary cannabinoids include but are not limited to the cannabinoids described in paragraphs [0111]-[0159] of US 2018/0221396 A1 and [0112]-[0160] US 2019/0142851 A1 as well as the disclosed exemplary embodiments, incorporated here by reference. Examples of cannabinoids within the context of this disclosure include the following molecules: Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBLV), Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA), Cannabinodiol (CBND), Cannabinodivarin (CBDV), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriol (CBT), Cannabitriolvarin (CBTV), 10-Ethoxy-9-hydroxy-delta-6a-tetrahydrocannabinol, Cannbicitran (CBT), Cannabiripsol (CBR), 8,9-Dihydroxy-delta-6a-tetrahydrocannabinol, Delta-8-tetrahydrocannabinol (A8-THC), Delta-8-tetrahydrocannabinolic acid (A8-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Delta-9-cis-tetrahydrocannabinol (cis-THC), Tryhydroxy-delta-9-tetrahydrocannabinol (triOH-THC), Dehydrocannabifuran (DCBF), and 3,4,5,6-Tetrahydro-7-hydroxy-alpha-alpha-2-trimethyl-9-n-propyl-2,6-metha-no-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed exemplary embodiments, incorporated here by reference. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10), 11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant. In one embodiment, an adrenergic drug is a norepinephrine transporter inhibitor. In one embodiment, an adrenergic drug is a vesicular monoamine transporter inhibitor. In one embodiment, an adrenergic drug is chosen from adrenaline, agmatine, amoxapine, aptazapine, atomoxetine, bupropion, clonidine, doxepin, duloxetine, esmirtazpine, mianserin, ketanserin, mirabegron, mirtazapine, norepinephrine, phentolamine, phenylephrine, piperoxan, reserpine, ritodrine, setiptiline, tesofensine, timolol, trazodone, trimipramine, or xylazine.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor. In one embodiment, a dopaminergic drug is a vesicular monoamine transporter inhibitor. In one embodiment, a dopaminergic drug is chosen from amineptine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencyclidine, phenethylamine, phenmetrazine, pimozide, piribedil, a psychostimulant, reserpine, risperidone, ropinirole, tetrabenazine, or thioridazine.

As used herein, the term "monoamine oxidase inhibitor" (MAOI) refers to a compound that blocks the actions of monoamine oxidase enzymes. In on embodiment, a MAOI inhibits the activity of one or both monoamine oxidase A and monoamine oxidase B. In one embodiment a MAOI is a reversible inhibitors of monoamine oxidase A. In one embodiment a MAOI is a drug chosen from isocarboxazid, phenelzine, or tranylcypromine.

In one embodiment, the compositions and methods disclosed herein include one or more purified erinacine molecules. In one embodiment, the compositions and methods disclosed herein comprise purified erinacine A. In one embodiment, the compositions and methods disclosed herein comprise erinacine B. In one embodiment, the compositions and methods disclosed herein comprise erinacine C. In one embodiment, the compositions and methods disclosed herein comprise erinacine D.

In one embodiment, the compositions and methods disclosed herein comprise erinacine E. In one embodiment, the compositions and methods disclosed herein comprise erinacine F. In one embodiment, the compositions and methods disclosed herein comprise erinacine G. In one embodiment, the compositions and methods disclosed herein comprise erinacine H. In one embodiment, the compositions and methods disclosed herein comprise erinacine I. In one embodiment, the compositions and methods disclosed herein comprise erinacine J. In one embodiment, the compositions and methods disclosed herein comprise erinacine K. In one embodiment, the compositions and methods disclosed herein comprise erinacine P. In one embodiment, the compositions and methods disclosed herein comprise erinacine Q. In one embodiment, the compositions and methods disclosed herein comprise erinacine R. In one embodiment, the compositions and methods disclosed herein comprise erinacine S.

In one embodiment, the compositions and methods disclosed herein include one or more purified hericenone molecules. In one embodiment, the compositions and methods disclosed herein comprise purified hericenone A. In one embodiment, the compositions and methods disclosed herein comprise purified hericenone B. In one embodiment, the compositions and methods disclosed herein comprise purified hericenone C. In one embodiment, the compositions and methods disclosed herein comprise purified hericenone D. In one embodiment, the compositions and methods disclosed herein comprise purified hericenone E. In one embodiment, the compositions and methods disclosed herein comprise purified hericenone F. In one embodiment, the compositions and methods disclosed herein comprise purified hericenone G. In one embodiment, the compositions and methods disclosed herein comprise purified hericenone H.

Exemplary compositions of a dialkyl tryptamine compounds of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone in exemplary molar ratios are shown in Table 3. A dialkyl tryptamine compound of the disclosure may be any one of the exemplary embodiments described above including their crystalline forms as disclosed herein.

TABLE 3

| Second Compound | Molar ratio of a dialkyl tryptamine compound:second compound | Molar ratio of a dialkyl tryptamine compound:second compound | Molar ratio of a dialkyl tryptamine compound:second compound |
| --- | --- | --- | --- |
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |

TABLE 3-continued

| Second Compound | Molar ratio of a dialkyl tryptamine compound:second compound | Molar ratio of a dialkyl tryptamine compound:second compound | Molar ratio of a dialkyl tryptamine compound:second compound |
| --- | --- | --- | --- |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

Exemplary pharmaceutical compositions of a dialkyl tryptamine compound of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and an excipient with exemplary molar ratios of a dialkyl tryptamine compound to the second compound are shown in Table 4. A dialkyl tryptamine compound of the disclosure may be any one of the exemplary embodiments described above including their crystalline forms as disclosed herein.

TABLE 4

| Second Compound | Molar ratio of a dialkyl tryptamine compound:second compound | Molar ratio of a dialkyl tryptamine compound:second compound | Molar ratio of a dialkyl tryptamine compound:second compound |
| --- | --- | --- | --- |
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |

TABLE 4-continued

| Second Compound | Molar ratio of a dialkyl tryptamine compound:second compound | Molar ratio of a dialkyl tryptamine compound:second compound | Molar ratio of a dialkyl tryptamine compound:second compound |
|---|---|---|---|
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

An "effective amount" or a "therapeutically effective amount" of a dialkyl tryptamine compound of the disclosure is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. A dialkyl tryptamine compound of the disclosure and pharmaceutical compositions containing it may be used in combination with other agents that are generally administered to a patient being treated for psychological and other disorders discussed above. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. Exemplary carriers include those that do not substantially alter the structure or activity of dialkyl tryptamine compound of the disclosure, nor produce undesirable biological effects or otherwise interact in a deleterious manner with any other component(s) of the pharmaceutical composition.

The pharmaceutical compositions of the disclosure may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, a dialkyl tryptamine compound of the disclosure may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. In some embodiments, the excipient is not water. In some embodiments, the excipient is not a solvent (e.g., EtOH, diethyl ether, ethyl acetate, or hydrocarbon-based solvents (e.g., hexanes). In some embodiments, the dosage form is substantially free of water and/or solvents, for example less than about 5% water by mass, less than 2% water by mass, less than 1% water by mass, less than 0.5% water by mass, or less than 0.1% water by mass.

Excipients or pharmaceutically acceptable adjuvants known in the pharmaceutical formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of dialkyl tryptamine compounds of the disclosure in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

Examples

General Synthesis Procedure:

At 0° C. to a reaction vial containing 3-(2-(dipropylamino)ethyl)-1H-indol-4-ol (0.4 mmol, 1 equiv) in anhydrous methylene chloride (8 mL) was added triethylamine (2 equiv) followed by corresponding acid chloride (1.5 equiv) in a dropwise manner. The resulting contents were then stirred at room temperature under nitrogen until the disappearance of the starting material (per thin layer chromatography) was observed. The typical reaction times were between 1.5 and 2 hours. The reaction contents were then diluted with methylene chloride (20 mL) and washed twice with cold water followed by brine. The resulting organic layer was dried using sodium sulfate and reduced under pressure to afford a residue which was dissolved in toluene (10 mL). To the resulting solution was added hydrochloric acid in ether (2 M, 1.1 equiv) dropwise and stirred at room temperature for 15 minutes. The contents were then reduced under pressure and the residue was suspended in ether and sonicated to afford solid which was then filtered and dried under vacuum to yield hydrochloride salt of desired DPT ester. In the case of sulfonates the residue after salt formation in toluene was subjected to column chromatography (methylene chloride/methanol) to obtain the desired compound. Note: For the carbonate derivative, the procedure above was adopted with methyl chloroformate (1.5 equiv) as starting material. The compounds listed below were prepared using this procedure. The structure of each compound was confirmed by $^1$H and $^{13}$C NMR.

N-(2-(4-((methoxycarbonyl)oxy)-1H-indol-3-yl)ethyl)-N-propylpropan-1-ammonium chloride

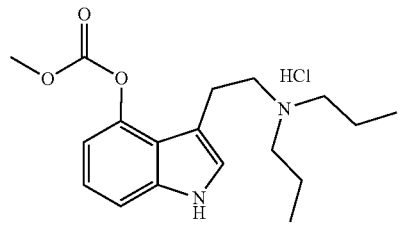 [SMILES: CCCN(CCC)CCc1c[nH]c2cccc(OC(=O)OC)c12 ; Cl]

$^1$H NMR (400 MHz, Deuterium Oxide) δ 7.39 (dd, J=8.3, 0.8 Hz, 1H), 7.26 (s, 1H), 7.18 (t, J=8.0 Hz, 1H), 6.91 (d, J=7.7 Hz, 1H), 3.90 (s, 3H), 3.37 (t, J=7.8 Hz, 2H), 3.15-2.98 (m, 10H), 1.64 (td, J=14.1, 13.4, 7.3 Hz, 4H), 0.86 (t, J=7.4 Hz, 6H); $^{13}$C NMR (101 MHz, DMSO-d$_6$) δ 154.43, 144.18, 139.06, 125.40, 121.87, 119.19, 111.71, 110.48, 56.16, 54.24, 53.63, 20.91, 17.25, 11.40.

N-(2-(4-(pivaloyloxy)-1H-indol-3-yl)ethyl)-N-propylpropan-1-ammonium chloride

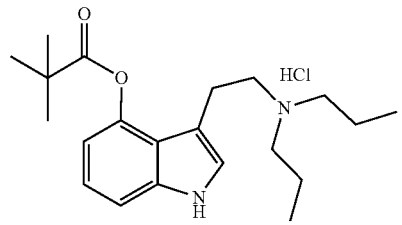 [SMILES: CCCN(CCC)CCc1c[nH]c2cccc(OC(=O)C(C)(C)C)c12 ; Cl]

$^1$H NMR (400 MHz, Deuterium Oxide) δ 7.38 (dd, J=8.2, 0.9 Hz, 1H), 7.26 (s, 1H), 7.18 (t, J=8.0 Hz, 1H), 6.73 (d, J=7.7 Hz, 1H), 3.47 (t, J=6.7 Hz, 2H), 3.10 (t, J=6.6 Hz, 2H), 3.01 (dt, J=9.6, 5.4 Hz, 4H), 1.55 (td, J=15.7, 15.1, 7.0 Hz, 4H), 1.36 (s, 9H), 0.79 (t, J=7.4 Hz, 6H); $^{13}$C NMR (101 MHz, Chloroform-d) δ 177.86, 144.49, 138.67, 122.98, 122.34, 119.40, 112.05, 109.79, 108.52, 54.42, 52.68, 39.37, 27.42, 21.07, 16.78, 11.12.

N-(2-(4-(benzoyloxy)-1H-indol-3-yl)ethyl)-N-propylpropan-1-ammonium chloride

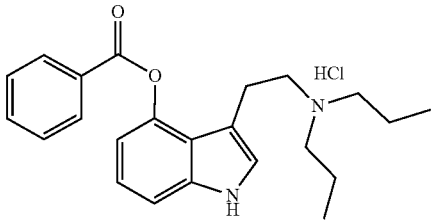 [SMILES: CCCN(CCC)CCc1c[nH]c2cccc(OC(=O)c3ccccc3)c12 ; Cl]

$^1$H NMR (400 MHz, Deuterium Oxide) δ 8.21 (d, J=7.4 Hz, 2H), 7.76 (t, J=7.5 Hz, 1H), 7.60 (t, J=7.8 Hz, 2H), 7.42 (d, J=8.1 Hz, 1H), 7.31-7.13 (m, 2H), 6.89 (d, J=7.5 Hz, 1H), 3.25-3.09 (m, 2H), 3.01-2.81 (m, 2H), 2.70 (dd, J=9.7, 4.9 Hz, 4H), 1.38 (dq, J=14.8, 7.4 Hz, 4H), 0.67 (t, J=7.4 Hz, 6H); $^{13}$C NMR (101 MHz, Chloroform-d) δ 165.70, 143.63, 138.73, 134.20, 130.27, 129.54, 129.14, 124.16, 122.29, 119.41, 112.40, 110.29, 108.07, 54.50, 53.78, 21.09, 16.70, 11.00.

N-(2-(4-((ethylsulfonyl)oxy)-1H-indol-3-yl)ethyl)-N-propylpropan-1-aminiumchloride

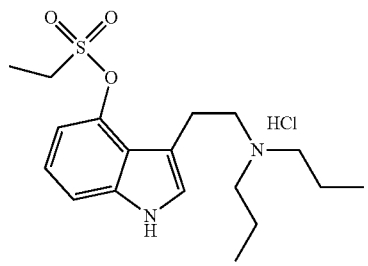 [SMILES: CCCN(CCC)CCc1c[nH]c2cccc(OS(=O)(=O)CC)c12 ; Cl]

¹H NMR (400 MHz, Deuterium Oxide) δ 7.45 (dd, J=8.3, 0.8 Hz, 1H), 7.30 (s, 1H), 7.19 (t, J=8.0 Hz, 1H), 7.03 (d, J=7.8 Hz, 1H), 3.60 (q, J=7.4 Hz, 2H), 3.48-3.34 (m, 2H), 3.34-3.19 (m, 2H), 3.07 (dd, J=10.4, 5.6 Hz, 4H), 1.62 (dq, J=13.8, 7.8, 6.8 Hz, 4H), 1.48 (t, J=7.4 Hz, 3H), 0.85 (t, J=7.4 Hz, 6H); ¹³C NMR (101 MHz, Chloroforrm-d) δ 142.71, 139.09, 125.04, 121.98, 119.65, 111.57, 110.87, 108.22, 54.47, 54.33, 45.25, 20.77, 17.11, 11.16, 8.21.

N-(2-(4-((phenylsulfonyl)oxy)-1H-indol-3-yl)ethyl)-N-propylpropan-1-ammonium chloride

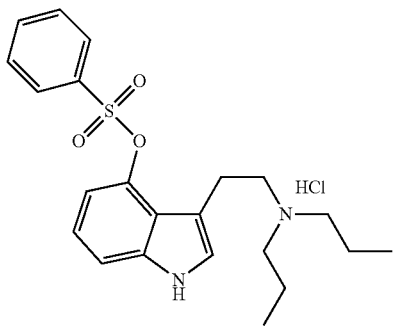 [SMILES: CCCN(CCC)CCc1c[nH]c2cccc(OS(=O)(=O)c3ccccc3)c12 ; Cl]

¹H NMR (400 MHz, Chloroform-d) δ 11.51 (s, 1H), 10.00 (s, 1H), 7.85 (dd, J=8.4, 1.3 Hz, 2H), 7.68 (t, J=7.5 Hz, 1H), 7.54 (t, J=7.8 Hz, 2H), 7.39 (d, J=8.1 Hz, 1H), 7.27 (s, 1H), 7.06 (d, J=1.9 Hz, 1H), 6.89 (t, J=8.0 Hz, 1H), 6.25 (d, J=7.8 Hz, 1H), 3.41 (dd, J=11.3, 5.1 Hz, 2H), 3.29 (dd, J=11.2, 5.1 Hz, 2H), 3.09 (dd, J=14.7, 7.3 Hz, 4H), 1.90 (dq, J=15.1, 7.4 Hz, 4H), 1.00 (t, J=7.3 Hz, 6H); ¹³C NMR (101 MHz, Chloroform-d) δ 142.72, 139.01, 135.80, 134.46, 129.31, 128.55, 125.11, 121.56, 119.78, 111.52, 111.45, 108.20, 54.55, 54.35, 20.73, 17.15, 11.18.

3-(2-(dipropylamino)ethyl)-1H-indol-4-yl benzoate

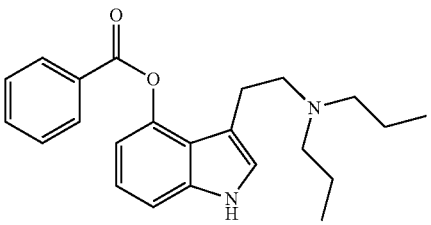 [SMILES: CCCN(CCC)CCc1c[nH]c2cccc(OC(=O)c3ccccc3)c12]

¹H NMR (400 MHz, Chloroform-d) δ 9.56 (s, 1H), 8.36-8.22 (m, 2H), 7.71 (t, J=7.4 Hz, 1H), 7.59 (t, J=7.7 Hz, 2H), 7.38 (d, J=8.1 Hz, 1H), 7.16 (t, J=7.9 Hz, 1H), 6.90 (d, J=2.3 Hz, 1H), 6.86 (d, J=7.6 Hz, 1H), 3.15 (dd, J=10.7, 5.5 Hz, 2H), 3.00 (dd, J=10.7, 5.6 Hz, 2H), 2.60-2.39 (m, 4H), 1.54 (dq, J=14.7, 7.3 Hz, 4H), 0.70 (t, J=7.4 Hz, 6H); ¹³C NMR (101 MHz, Chloroform-d) δ 165.73, 143.68, 138.72, 134.16, 130.28, 129.54, 129.10, 124.04, 122.26, 119.47, 112.39, 110.21, 108.50, 54.55, 53.93, 21.30, 16.98, 11.07.

3-(2-(dipropylamino)ethyl)-1H-indol-4-yl ethanesulfonate

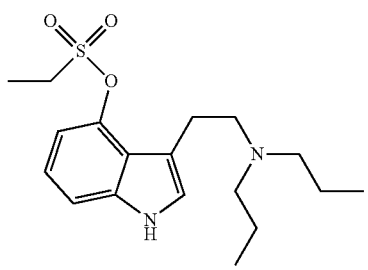 [SMILES: CCCN(CCC)CCc1c[nH]c2cccc(OS(=O)(=O)CC)c12]

¹H NMR (400 MHz, Chloroform-d) δ 8.86 (s, 1H), 7.34 (dd, J=8.1, 0.9 Hz, 1H), 7.12 (t, J=7.9 Hz, 1H), 7.06-6.92 (m, 2H), 3.42 (q, J=7.5 Hz, 2H), 3.32-3.17 (m, 2H), 3.12-2.91 (m, 2H), 2.75 (t, J=7.8 Hz, 4H), 1.67 (h, J=7.2 Hz, 4H), 1.56 (t, J=7.5 Hz, 3H), 0.93 (t, J=7.4 Hz, 6H).

REFERENCES

Carhart-Harris, R. L. & Goodwin, G. M. (2017). *Neuropsychopharmacology*, 42, 2105-2113.

Dinis-Oliveira, R. J. (2017). *Drug Metab. Rev.* 49, 84-91.

Johnson, M. W. & Griffiths, R. R. (2017). *Neurotherapeutics* 14, 734-740.

C. Lenz, J. Wick and D. Hoffmeister, *J. Nat. Prod.*, 2017, 80, 2835-2838.

A. M. Sherwood, A. L. Halberstadt, A. K. Klein, J. D. McCorvy, K. W. Kaylo, R. B. Kargbo and P. Meisenheimer, *J. Nat. Prod.*, Article ASAP, DOI: 10.1021/acs.jnatprod.9b01061.

Sheldrick, G. M. (2008). *Acta Cryst.* A64, 112-122.

Sheldrick, G. M. (2015). *Acta Cryst.* C71, 3-8.

Dolomanov, O. V., Bourhis, L. J., Gildea, R. J., Howard, J. A. K. & Puschmann, H. (2009). *J. Appl. Cryst.* 42, 339-341.

The claimed disclosure is:

1. A compound of formula (I):

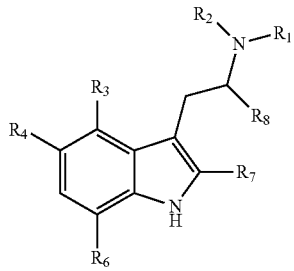

wherein
$R_1$ and $R_2$ are each n-propyl;
$R_3$ is —OC(O)OR$_5$;
$R_4$ is hydrogen;
$R_5$ is methyl; and
$R_6$, $R_7$ and $R_8$ are each hydrogen;
wherein the compound of formula (I) is a pharmaceutically acceptable acid-addition salt thereof, and wherein the acid-addition salt is hydrochloric acid.

2. A compound of formula (I):

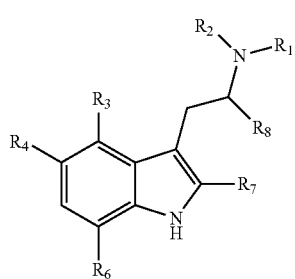

wherein
$R_1$ and $R_2$ are each n-propyl;
$R_3$ is —OC(O)OR$_5$;
$R_4$ is hydrogen;
$R_5$ methyl; and
$R_6$, $R_7$ and $R_8$ are each hydrogen;
wherein the compound of formula (I) is a pharmaceutically acceptable acid-addition salt thereof;
wherein the acid-addition salt is hydrochloric acid; and
wherein the purity of the compound of formula (I) is greater than 98%.

* * * * *